United States Patent [19]

Shillington

[11] Patent Number: 5,154,345
[45] Date of Patent: Oct. 13, 1992

[54] SECURE CONTAINER FOR DISPOSABLE SHARPS

[75] Inventor: Richard A. Shillington, Leucadia, Calif.

[73] Assignee: Med-Safe Systems, Inc., Leucadia, Calif.

[21] Appl. No.: 729,058

[22] Filed: Jul. 12, 1991

Related U.S. Application Data

[63] Continuation of Ser. No. 446,121, Dec. 5, 1989, abandoned.

[51] Int. Cl.$^5$ ............................................. B65F 1/16
[52] U.S. Cl. ............................. 232/44; 220/908; 220/740; 220/481; 220/254; 206/366
[58] Field of Search ............... 220/254, 480, 481, 630, 220/85 H, 252, 908, 910, 740; 206/365, 366, 370; 232/43.1, 43.3, 43.5, 44, 47, 62, 43.2

[56] References Cited

U.S. PATENT DOCUMENTS

| | | | |
|---|---|---|---|
| 1,333,051 | 3/1920 | Young | 220/252 |
| 1,638,360 | 8/1927 | Olson | 220/252 |
| 2,986,328 | 5/1961 | Delas | 232/43.1 |
| 4,453,648 | 6/1984 | Harris et al. | 206/370 |
| 4,702,385 | 10/1987 | Shillington et al. | 220/408 |
| 4,736,860 | 4/1988 | Bemis | 220/252 |
| 4,804,090 | 2/1989 | Schuh et al. | 206/366 |
| 4,809,850 | 3/1989 | Laible et al. | 206/366 |
| 4,828,107 | 5/1989 | Spencer | 206/366 |
| 4,850,484 | 7/1989 | Denman | 220/480 |
| 5,046,614 | 9/1991 | Torres et al. | 220/252 |

FOREIGN PATENT DOCUMENTS 473199  10/1937  United Kingdom ............... 220/254

Primary Examiner—Stephen Marcus
Assistant Examiner—S. Castellano
Attorney, Agent, or Firm—Baker, Maxham, Jester & Meador

[57] ABSTRACT

A secure disposable container assembly for medical sharps and waste comprises the combination of a substantially rigid box-like lower housing defined by upstanding front, back, and side walls terminating with a top having an upwardly extending rectangular opening for providing access to the housing, and a semi-cylindrical top curving about a generally horizontal axis secured along one edge of said top by a hinge and secured along the other edge by locking tabs for permanent securement thereto, an elongated horizontally extending access opening in said top for receiving a disposable syringe or the like, and a pivotable closure for said opening pivotably mounted about said axis within the top and having a receptacle area normally exposed to said access opening in a first position for receiving a disposed article and a curved surface for covering the access opening upon pivoting from said first position to a second position for dumping the article into said housing.

18 Claims, 3 Drawing Sheets

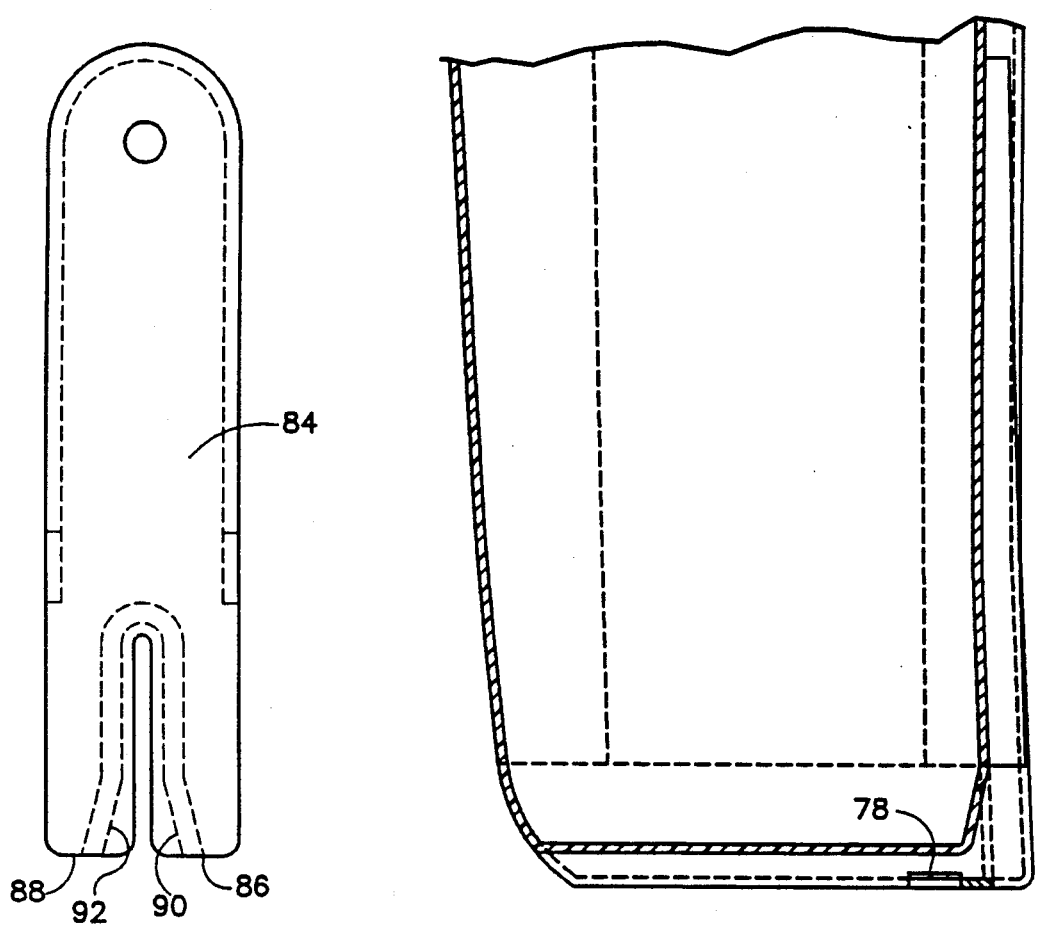
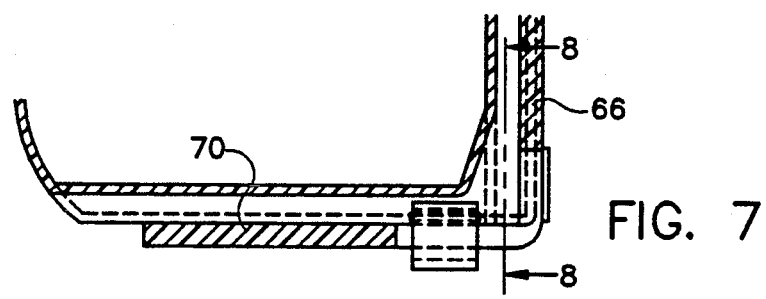
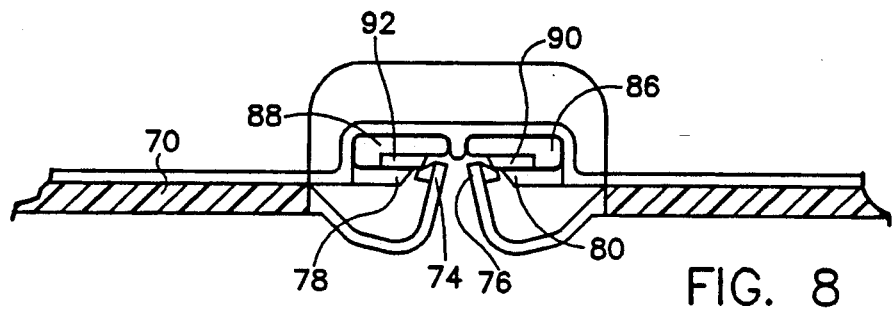

SECURE CONTAINER FOR DISPOSABLE SHARPS

REFERENCE TO RELATED APPLICATION

The present application is a continuation of my co-pending application Ser. No. 07/446,121, filed Dec. 5, 1989, entitled "A Secure Container For Disposable Sharps", abandoned.

BACKGROUND OF THE INVENTION

The present invention relates to containers for disposable hospital sharps and waste, and pertains particularly to a secure disposable container assembly for disposition of hospital sharps, objects and wastes.

Hospitals and clinics use great quantities of sharps, such as needles, syringes, surgical blades, and the like, that are disposed of rather than cleaned and reused. It is necessary that the sharps be disposed of in a manner that prevents them being reused without sterilization. In particular, it is necessary to keep them from falling into the hands of those, such as drug users and the like, that are likely to use them without proper sterilization.

Numerous containers have been developed in recent years, which are reasonably secure and disposable for receiving and disposing of hospital sharps, wastes and the like. Many of these containers however do not provide adequate security against pilfering of used syringes and the like from such containers. While containers have been developed which cannot readily be reopened and articles cannot be easily removed therefrom, such containers must be kept in a secure place to prevent unauthorized removal.

It is essential that access openings into the containers be easy and convenient to use, yet prevent access thereto for removal of articles. This requires that the opening be adequate in size to receive the article, be conveniently located and that it has a suitable closure to prevent removal of articles. It is also necessary that the article be received into the container without undue action by the user. While many excellent closures exist, improvements are desirable.

In prior U.S. Pat. No. 4,702,385, of which I am co-inventor, we disclose a security mounting device for disposable containers. That device includes a metal mounting bracket, with a complex metal latching arrangement for securely latching a disposable container within a secured container housing. While that prior device is suitable for many applications, certain improvements are desirable.

It is, therefore, desirable that an improved securable disposable container assembly be provided.

SUMMARY AND OBJECTS OF THE INVENTION

It is the primary object of the present invention to provide an improved securable disposable container assembly.

In accordance with a primary aspect of the present invention, a secure disposable container assembly comprises a housing for securely mounting to a support member, and having an access opening in a top front for receiving a disposable article and preventing access to the interior of the container by the human hand. Means are provided for locking the housing to a support bracket to prevent removal of the container.

BRIEF DESCRIPTION OF THE DRAWING

The above and other objects and advantages of the present invention will become apparent from the following description when read in conjunction with the accompanying drawings wherein:

FIG. 6 is a partial side elevation view in section;

FIG. 7 is a partial side elevation view in section showing the container mount;

FIG. 8 is a view taken generally on line 8—8 of FIG. 7; and

FIG. 9 is a top plan view of the latch release key.

DETAILED DESCRIPTION OF A PREFERRED EMBODIMENT

Figure 1:
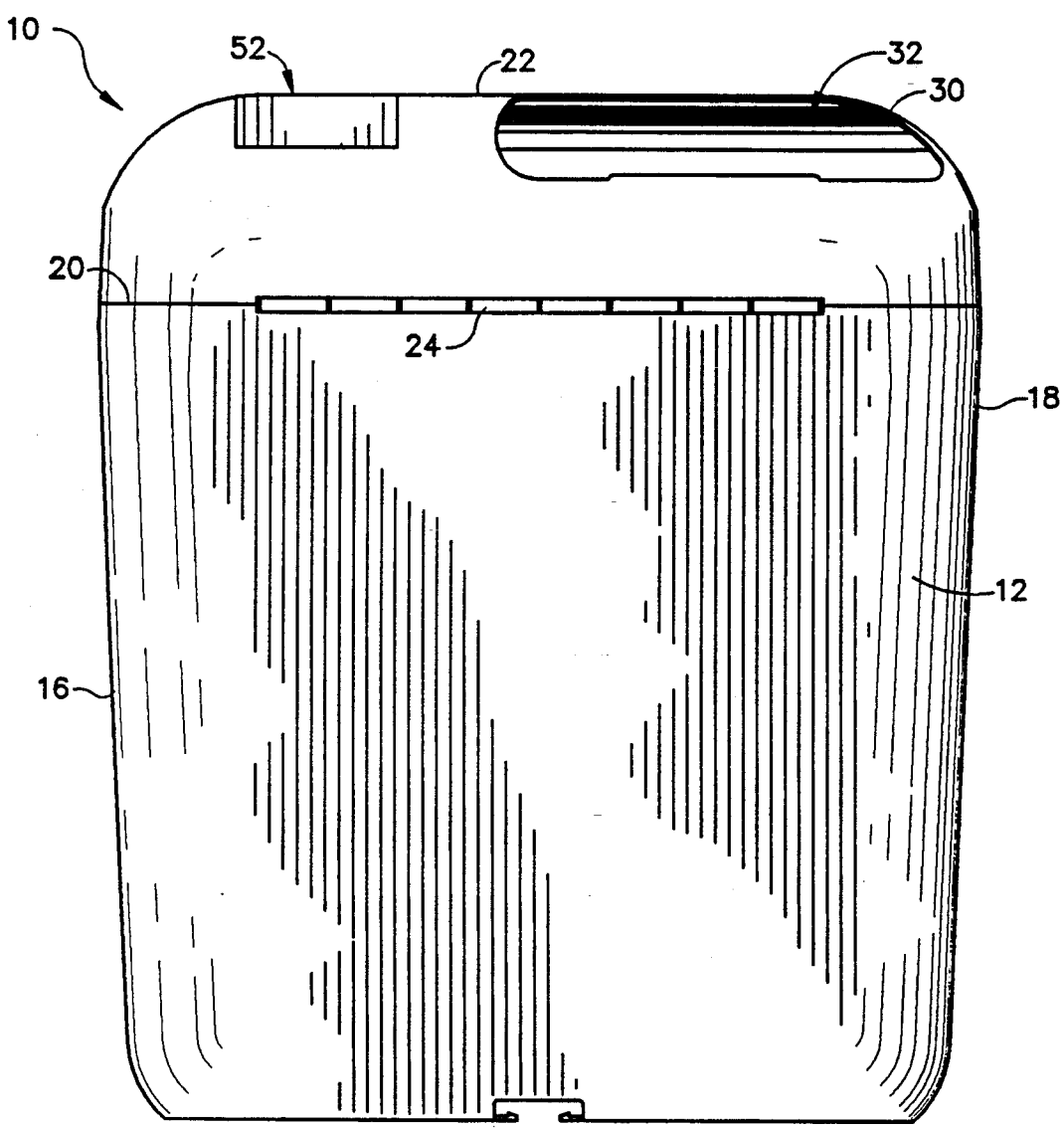
FIG. 1 is a front elevation view of an exemplary embodiment of the invention.

Referring to FIG. 1 of the drawing, there is illustrated an exemplary embodiment of the invention, which comprises a generally rectangular box-like housing, designated generally by the numeral 10, and formed of the usual plastic material for such containers. The housing in its preferred form is formed of a lower substantially rectangular shell, having a front wall or panel 12 and a back wall or panel 14 (FIG. 5) defining front and back walls, and further including opposed side walls 16 and 18, all terminating at a top rectangular peripheral edge 20. A generally semi-circular top shell 22 is hinged at 24 to the top front edge of the rectangular shell 10.

The top 22 and bottom may be molded together with a live hinge or they be molded separately and utilize a snap lock hinge 24, as generally illustrated. A live hinge is a thin strip of the housing material connecting the two members and allowing them to pivot relative to one another. The hinge comprises a plurality of upwardly directed hooks on one member for hooking under a plurality of hinge pins formed or mounted in a plurality of tabs on the other member. The hooks have detents into which the hinge pin or pins snap into. A tab lock assembly includes tabs 26 on the top and tab sockets on the upper or top back edge of the container to permanently lock the top 22 in the covering position as shown.

Figure 2:
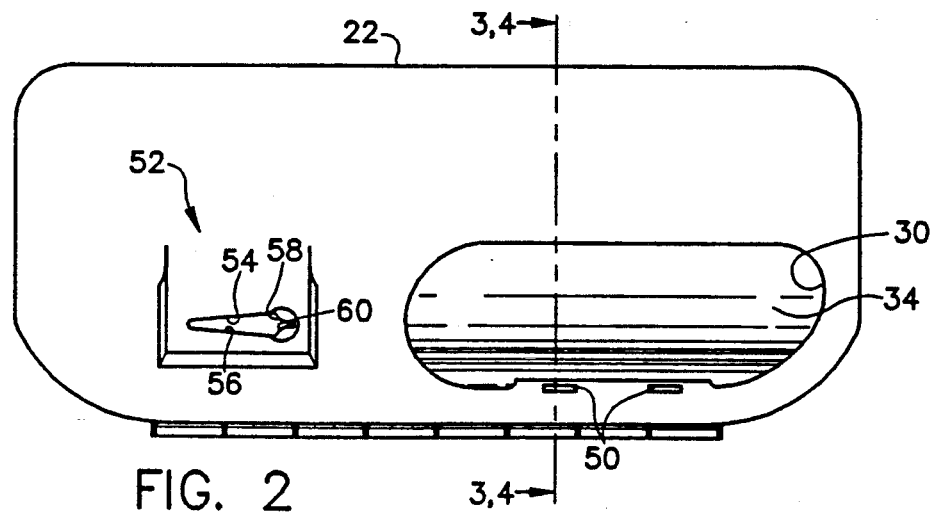
FIG. 2 is a top plan view of the embodiment of FIG. 1.

The container top and bottom is preferably blow molded of a suitable plastic, and preferably formed with a slight taper from top to bottom to enable stacking for ease of shipment. The top 22 has a generally semi-cylindrical configuration about a horizontal axis, about which a pivoting closure member is mounted. Referring to FIG. 2, the top 22 is provided with a top front opening 30 of a generally elongated configuration having circular or oval ends. This opening is formed in the upper front one side of the top extending approximately one-half the length of the top. This opening is designed to receive syringes and the like for disposal and to secure the syringes against unauthorized retrieval.

Figure 3:
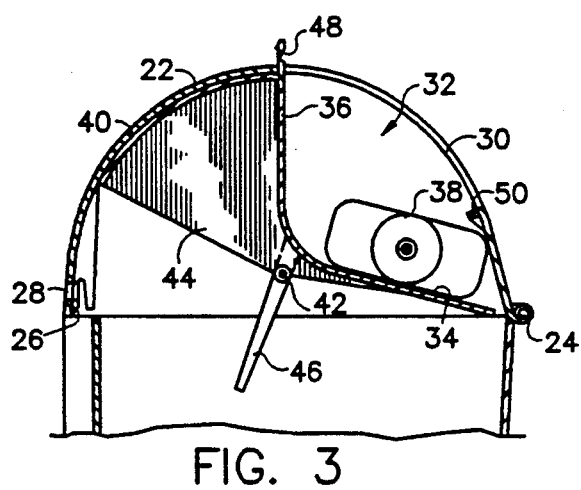
FIG. 3 is a detailed partial view in section taken on line 3—3 of FIG. 2.
Figure 4:
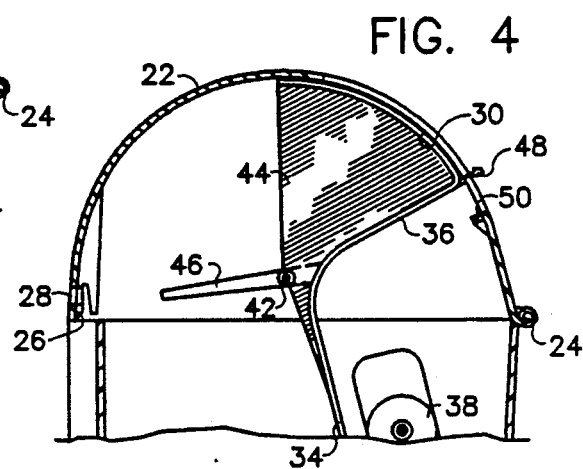
FIG. 4 is a detailed partial view in section taken on line 4—4 of FIG. 3.

The opening is closed by a pivoting closure member or unit, as illustrated in FIGS. 3-4, of a substantially unitary structure designated generally by the numeral 32. The closure member has a generally horizontal face or ledge portion 34 disposed below the opening 30, and a substantially vertical face portion 36 forming a continuation of the face 34, extending upward at approximately a one-hundred five degree angle. These faces together form a combination closure and receiving support for disposable articles, such as a syringe or the like 38 as illustrated. The closure unit 32 includes a curved surface portion 40 extending backward from the upper or top edge of the face portion 36, thereby forming a closure for extending over the opening 30 when the closure member pivots about horizontal axis 42 for dumping article 38. An end wall portion 44 of the closure member adds strength and rigidity to the closure unit.

The closure unit 32 is mounted for pivotal movement about a pair of pins, one at each end, which are rotatably mounted in snap in journals in the ends of the top. A counter weight 46 formed as an extending piece of the closure unit 32 extends downward from the axis of the pivot pins and pivot axis of the unit, and biases the closure unit to its normally closed article receiving position. Once the container has been filled, the closure is forced or rotated to its closed position, such that curved closure portion 40 extends over the opening 30, and lock tabs 48 on an upper portion of the closure panel 36 extend into and lock into lock slots or sockets 50, forming in a small horizontal lip at the forward edge of the housing opening. This essentially permanently locks the container in its closed position for disposal.

In normal operation, to dispose of a syringe as viewed in FIG. 2, the syringe is inserted into the top opening, with the needle extending toward the left to extend inside and underneath the top of the housing, such that the body of the syringe is placed on the horizontal closure surface 34, as seen in FIG. 3. The weight of the syringe overcomes the counterweight and tilts the closure member to dump the syringe into the container, as illustrated at FIG. 4. At the same time, the closure surface 40 moves forward and covers the opening 30 to prevent the insertion of a hand or the like for the removal of articles from the container.

If it is desirable to remove the needle to either reuse the syringe or prior to disposing of the syringe, a needle removal slot, designed generally by the numeral 52, is formed in the upper portion of the top for this purpose. This needle removal slot has a generally tear-drop configuration converging from a larger diameter at one end to a smaller diameter at the other. The slot has a pair of opposed tapered side walls 54 and 56, which act as wrench surfaces for engaging the side of a needle hub for applying torque for unthreading the needle. A pair of opposed fingernail like edges 58 and 60 are provided at the larger end thereof for engaging between the threaded end of the shank of the needle and the syringe body to enable it to be pulled out of the syringe body.

Figure 5:
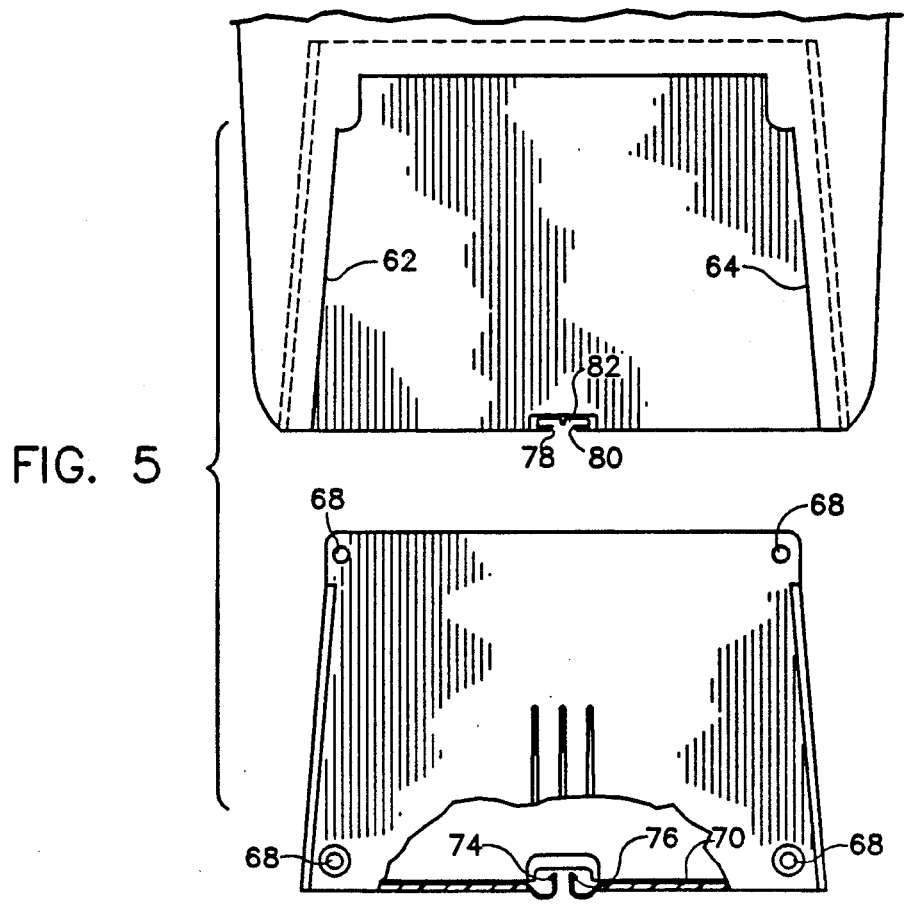
FIG. 5 is a detailed partial back view of the container with portions broken away to reveal details.

Referring to FIGS. 5-8, the container is designed for wall mounting by means of a lockable bracket that is preferably permanently attached to a wall or suitable wall like structure. The back of the container, as shown in FIGS. 5 and 6, is provided with a recess having overlapped side portions 62 and 64 that receive a vertically extending back panel 66 secured to a wall or like vertical surface by means of suitable screws or the like in a plurality of holes 68. The bracket 66 includes a forwardly extending support shelf or surface 70, which is formed with a pair of lock hooks 74 and 76 at the center and at a position closely adjacent the back panel portion. These finger hooks or locks are designed to receive and latch to latching fingers 78 and 80 formed at the back end of a channel 82 formed along the bottom of the container.

The channel 82 is designed to receive latch releasing or unlocking key, as illustrated in FIGS. 8 and 9, which comprises a main body member 84 having a pair of fingers 86 and 88 at a forward end thereof. The fingers are provided with camming surfaces 90 and 92 that extend downward for engaging and camming the lock hooks or fingers 74 and 76 out of latching engagement with latching fingers 78 and 80, as shown in FIG. 9. Thus, the container can be locked to the support bracket 66, and when ready for disposal or removal, a key 84 is selected and inserted in the slot 82 for engaging and releasing the lock or latch. The container can then be removed from the bracket and disposed of, and a new container mounted.

While I have illustrated and described my invention by means of specific embodiments, it should be understood that numerous changes and modifications may be made therein without departing from the spirit and scope of the invention as defined in the appended claims. I further assert and sincerely believe that the above specification contains a written description of the invention and the manner and process of making and using it, in such full, clear, concise, and exact terms as to enable any person skilled in the art to which it pertains, or with which it is most nearly concerned, to make and use the same, and further that it sets forth the best mode contemplated by me for carrying out the invention.

I claim:

1. A secure disposable container assembly having a self dumping closure for disposal of hospital sharps, comprising:

a generally box-like enclosed housing having a top cover with a portion curving about a generally horizontal axis having a front side and a back side;

an access opening in said top cover for receiving a disposable article; and a self-dumping closure for said access opening pivotably mounted within said top cover for pivoting about said horizontal axis between a normally closed position for receiving said disposable article and a dump position, means for biasing said self-dumping closure to said normally closed position, said self-dumping closure having support means defining a receptacle area having a width about equal to the radius of the top cover disposed and extending radially outward from proximate said axis to a wall of said top cover solely on said front side of said axis, means including a curved surface and a sloping surface joined to and extending upwardly from said receptacle area proximate said axis to said curved surface disposed above said generally horizontal axis and on the front side of the axis for diverting said article from said back side to said receptacle area, said self-dumping closure pivoting in response to said article on said receptacle area to said dump position for automatically dumping said article, wherein said receptacle area is normally exposed to and covering said access opening in said normally closed position and said curved surface is moved to and covering said access opening upon pivoting of said self-dumping closure from said normally closed position to said dump position.

2. A secure disposable container assembly according to claim 1 wherein said access opening is an elongated horizontally extending slot.

3. A secure disposable container assembly according to claim 2 wherein said access opening is positioned on said front side of said top cover and extends to proximate the center thereof.

4. A secure disposable container assembly according to claim 1 wherein said closure comprises an elongated member extending the length of said top cover, and wherein said receptacle area is defined by a substantially horizontally extending support surface and said curved surface is defined by an adjacent semi-cylindrical portion extending along the axis thereof.

5. A secure disposable container assembly according to claim 1 wherein said housing comprises a substantially rigid bottom shell defined by upstanding substantially rectangular walls terminating in a generally rectangular rim defining an upwardly extending top opening, said top cover is defined by a substantially semi-cylindrical top shell hinged along an edge to an edge of said rim for covering said top opening, and having locking tabs for locking said top shell in position covering said top opening.

6. A secure disposable container assembly according to claim 5 wherein said housing having a back wall having mounting means for mounting on a vertical support means, and a bottom having a latching slot for engagement by a mount latch, and slide means engaging the bottom of said housing for releasing said latch.

7. A secure disposable container assembly according to claim 1 wherein said self-dumping closure includes locking means for permanently locking said closure in said dump position.

8. A secure disposable container assembly according to claim 7 wherein said locking means comprises tabs on said closure for engaging slots in said top cover at a lower edge of said access opening.

9. A secure disposable container assembly according to claim 8 wherein said closure comprises an elongated member extending the length of said top cover, and wherein said receptacle area is defined by a substantially horizontally extending support surface and said curved surface is defined by an adjacent semi-cylindrical portion extending along the axis thereto.

10. A secure disposable container assembly for disposal of hospital sharps, comprising:
a generally box-like enclosed housing comprising a substantially rigid bottom shell defined by upstanding substantially rectangular walls terminating in a generally rectangular rim defining an upwardly extending top opening, a top cover defined by a substantially semi-cylindrical top shell curving about a generally horizontal axis having a front side and a back side, said top shell hinged along an edge to an edge of said rim for covering said top opening, locking tabs for locking said top shell in position covering said top opening;
an elongated horizontally extending access opening in said top shell for receiving a disposable article; and
a pivotable closure for said access opening pivotably mounted about said horizontal axis within said top shell and having a substantially horizontal receptacle area having a width about equal to the radius of said top cover extending from proximate and solely on said front side of said axis to a wall of said top shell and normally exposed to said access opening in a first position for receiving said disposable article and an upwardly extending surface joining said substantially horizontal receptacle area at and extending upwardly from proximate said axis for diverting said disposable article to said receptacle area and said upwardly extending surface joining a curved surface disposed and extending above and on the back side of said axis for covering said access opening upon pivoting in response to the weight of said disposable article on said receptacle area from said first position to a second position for dumping said article into said housing.

11. A secure disposable container assembly according to claim 10 wherein said closure comprises an elongated member extending the length of said top, and said curved surface is defined by an adjacent semi-cylindrical portion extending along the axis thereof.

12. A secure disposable container assembly according to claim 11 wherein said access opening is an elongated horizontally extending slot.

13. A secure disposable container assembly according to claim 12 wherein said access opening is positioned on the front side of the axis of said top shell and extends to proximate the center thereof.

14. A secure disposable container assembly according to claim 13 wherein said pivotable closure includes locking means for permanently locking said closure in said second position.

15. A secure disposable container assembly for medical sharps comprising in combination:
a substantially rigid box-like lower housing defined by upstanding front, back, and side walls terminating with top edges defining an upwardly extending top opening, and a semi-cylindrical top cover defined by a substantially semi-cylindrical top shell curving about a generally horizontal axis having a front side and a back side, said top shell secured along one edge of said top edges by hinge means and secured along another edge by locking tabs for permanent securement thereto;
an elongated horizontally extending access opening positioned on said front side in said top shell and extending to proximate the center thereof for receiving a disposable article; and
a pivotable closure for said access opening pivotably mounted about said axis within said top shell and having a substantially horizontal receptacle area having a width about equal to the radius of said top shell disposed and extending substantially horizontally from proximate said axis solely on said front side of said axis to a wall of said top shell and normally exposed to said access opening in a first position for receiving said article and an upwardly extending surface joining said receptacle area and extending upwardly from proximate said axis and joining a curved surface disposed above and on the back side of said axis for covering said access opening upon pivoting from said first position to a second position in response to the weight of said article on said receptacle area for dumping said article into said housing.

16. A secure disposable container assembly according to claim 15 wherein said closure comprises an elongated member extending the length of said top shell, and wherein said receptacle area is defined by a substantially horizontal support surface, and said curved portion is defined by an adjacent semi-cylindrical portion extending along the axis thereof.

17. A secure disposable container assembly according to claim 16 wherein said closure includes locking tabs for engaging slots in said top shell adjacent said access opening for permanently locking said closure in said second position.

18. A secure disposable container assembly according to claim 16 wherein said housing having a back wall having mounting means for mounting on a vertically extending support panel, and a bottom having a latching slot for engagement by a pair of latch fingers, and latch release means for extending along said slot for releasing said latch fingers.

* * * * *